United States Patent [19]

Bruynes et al.

[11] 4,379,923

[45] Apr. 12, 1983

[54] PREPARATION OF 7-ACYLAMINO-3-(THIO-SUBSTITUTED)-METHYL 3-CEPHEM-4-CARBOXYLIC ACID-1-OXIDE DERIVATIVES

[75] Inventors: Cornelis A. Bruynes, Koudekerk; Theodorus K. Jurriens, Delft, both of Netherlands

[73] Assignee: Gist-Brocades N.V., Delft, Netherlands

[21] Appl. No.: 297,214

[22] Filed: Aug. 28, 1981

[30] Foreign Application Priority Data

Sep. 5, 1980 [NL] Netherlands .................. 8005041

[51] Int. Cl.³ ........................................... C07D 501/04
[52] U.S. Cl. ....................................... 544/26; 544/21; 544/27
[58] Field of Search ................ 424/246; 544/16, 27, 544/26, 22

[56] References Cited

U.S. PATENT DOCUMENTS 3,658,799 4/1972 Eardley et al. .................. 544/16
4,148,817 4/1979 Wright ............................. 544/16
4,266,049 9/1981 Bonjooklian .................... 544/16
4,284,766 8/1981 Laing et al. ..................... 544/16

*Primary Examiner*—Nicholas S. Rizzo
*Attorney, Agent, or Firm*—Hammond & Littell, Weissenberger and Muserlian

[57] ABSTRACT

A novel process for the preparation of 7-acylamino-3-(thio-substituted)-methyl-3-cephem-4-carboxylic acid 1-oxide derivatives comprising reacting a 7-acylamino-3-bromomethyl-3-cephem-4-carboxylic acid-1-oxide derivative with a silylated thiol of the formula $$R-S-Si(CH_3)_3 \qquad I$$

wherein R is an organic group, preferably a 5- or 6-membered heterocyclic group, which reaction is preferably carried out in the presence of an inert organic solvent at a temperature between −20° and 80° C. to obtain the corresponding 7-acylamino-3-(R-thiomethyl)-3-cephem-4-carboxylic acid-1-oxide derivatives, which are valuable intermediates in methods for the preparation of therapeutically active cephalosporins.

6 Claims, No Drawings

PREPARATION OF 7-ACYLAMINO-3-(THIO-SUBSTITUTED)-METHYL 3-CEPHEM-4-CARBOXYLIC ACID-1-OXIDE DERIVATIVES

STATE OF THE ART

In one of the known methods for the introduction of a thio-substituent to the 3-methyl group of cephalosporanic acid derivatives, 7-amino-3-acetoxymethyl-3-cephem-4-carboxylic acid is reacted with the appropriate thiol, but the starting material for this process is expensive and the yields of these reactions are generally not very high. In another known method for the preparation of such thio-substituted derivatives, the starting materials are deacetoxy-cephalosporanic acid derivatives which can be obtained from 7-aminopenicillanic acid-1-oxide derivatives by a ring-enlargement reaction and these deacetoxycephalosporanic acid derivatives can be converted in a known manner to 7-acylamino-3-bromomethyl-3-cephem-4-carboxylic acid-1-oxide derivatives which can be used for the preparation of corresponding 3-(thiosubstituted)-methyl derivatives.

For that purpose, the 3-bromomethyl compounds are reacted with the sodium or potassium salt of the appropriate thiol or with the thiol itself in the presence of an acid-binding agent, for example triethylamine as illustrated in British Pat. No. 1,326,531. A drawback to this process is that these reactions are carried out under alkaline conditions which result in a highly colored reaction mixture indicating the formation of by-products and yields of these reactions are moderate. Moreover, when sodium or potassium salts are used, the reactions proceed under heterogeneous conditions and, therefore, rather long reaction times are required.

OBJECTS OF THE INVENTION

It is an object of the invention to avoid the disadvantage of these known methods for the introduction of a thio-substituent in the 3-methyl group of cephalosporanic acid derivatives by reacting a 7-acylamino-3-bromomethyl-3-cephem-4-carboxylic acid-1-oxide derivative with a trimethylsilylated thiol, i.e. a thiol wherein the hydrogen atom of the mercapto group has been replaced by a trimethylsilyl group.

It is another object of the invention to provide a novel process for the preparation of 7-acylamino-3-(thiosubstituted)-methyl-3-cephem-4-carboxylic acid compounds under homogenous and smooth reaction conditions with virtually quantitative yields.

These and other objects and advantages of the invention will become obvious from the following detailed description.

THE INVENTION

The novel process of the invention for the preparation of 7-acylamino-3-(thio-substituted)-methyl-3-cephem-4-carboxylic acid-1-oxide derivatives comprising reacting a 7-acylamino-3-bromomethyl-3-cephem-4-carboxylic acid-1-oxide derivative with a silylated thiol of the formula

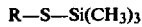

R—S—Si(CH$_3$)$_3$  I wherein R is an organic group to obtain the corresponding 7-acylamino-3-(R-thiomethyl)-3-cephem-4-carboxylic acid-1-oxide.

The process of the invention is preferably carried out by reacting a 7-acylamino-3-bromomethyl-3-cephem-4-carboxylic acid-1-oxide derivative with a silylated thiol of the formula I, preferably in the presence of an inert organic solvent at a temperature between −20° and 80° C., most preferably between 0° and 50° C.

Examples of suitable solvents are hydrocarbons such as benzene, toluene, xylene and petroleum ether; chlorinated hydrocarbons such as chlorobenzene, dichloromethane, chloroform, carbon tetrachloride and 1,2-dichloroethane; esters such as ethyl acetate and butyl acetate; acetonitrile or mixtures of one or more of said solvents.

The 3-bromomethyl cephalosporanic acid starting material can be used in the form of their free acids as well as in the form of esters thereof. Normal carbon esters such as, for example, the methyl, t-butyl, 2-bromoethyl, 2,2,2-trichloroethyl; benzhydryl, benzyl ,4-nitrobenzyl, 4-methoxybenzyl esters as well as silyl esters such as, for example, the trimethylsilyl, tri-n-propylsilyl, t-butyldimethylsilyl, trihexylsilyl, chloromethyldimethylsilyl esters may be used.

The 7-acylamino side chain in the 3-bromomethyl cephalosporanic acid starting material can be any acylamino group known in cephalosporin chemistry, provided this group does not interfere with the process of the invention. Suitable acylamino groups are, for example, phenylacetamido, phenoxyacetamido, benzamido and formamido.

Suitable 7-acylamino-3-bromomethyl-3-cephem-4-carboxylic acid-1-oxide starting materials for use in the process of the invention are, for example: t-butyl 7-benzamido-3-bromomethyl-3-cephem-4-carboxylate-1-oxide, t-butyl 7-phenylacetamido-3-bromomethyl-3-cephem-4-carboxylate-1-oxide, 2-bromoethyl 7-phenylacetamido-3-bromomethyl-3-cephem-4-carboxylate-1-oxide, t-butyl 7-formamido-3-bromomethyl-3-cephem-4-carboxylate-1-oxide, 2,2,2-trichloroethyl 7-formamido-3-bromomethyl-3-cephem-4-carboxylate-1-oxide, methyl 7-phenylacetamido-3-bromomethyl-3-cephem-4-carboxylate-1-oxide, t-butyl 7-phenoxyacetamido-3-bromomethyl-3-cephem-4-carboxylate-1-oxide, 2,2,2-trichloroethyl 7-phenoxyacetamido-3-bromomethyl-3-cephem-4-carboxylate-1-oxide, benzhydryl 7-phenylacetamido-3-bromomethyl-3-cephem-4-carboxylate-1-oxide, benzyl 7-benzamido-3-bromomethyl-3-cephem-4-carboxylate-1-oxide, 4-nitrobenzyl 7-phenylacetamido-3-bromomethyl-3-cephem-4-carboxylate-1-oxide, 4-methoxybenzyl 7-phenylacetamido-3-bromomethyl-3-cephem-4-carboxylate-1-oxide, trimethylsilyl 7-phenylacetamido-3-bromomethyl-3-cephem-4-carboxylate-1-oxide, methyl 7-benzamido-3-bromomethyl-3-cephem-4-carboxylate-1-oxide, methyl 7-phenoxyacetamido-3-bromomethyl-3-cephem-4-carboxylate-1-oxide, methyl 7-formamido-3-bromomethyl-3-cephem-4-carboxylate-1-oxide, trimethylsilyl 7-phenoxyacetamido-3-bromomethyl-3-cephem-4-carboxylate-1-oxide, trimethylsilyl 7-formamido-3-bromomethyl-3-cephem-4-carboxylate-1-oxide, trimethylsilyl 7-benzamido-3-bromomethyl-3-cephem-4-carboxylate-1-oxide, tri-n-propylsilyl 7-benzamido-3-bromomethyl-3-cephem-4-carboxylate-1-oxide, t-butyldimethylsilyl 7-benzamido-3-bromomethyl-3-cephem-4-carboxylate-1-oxide, trihexylsilyl 7-formamido-3-bromomethyl-3-cephem-4-carboxylate-1-oxide, t-butyldimethylsilyl 7-phenoxyacetamido-3-bromomethyl-3-cephem-4-carboxylate-1-oxide, chloromethyldimethylsilyl 7-phenoxyacetamido-3- bromomethyl-3-cephem-4-carboxylate-1-oxide, 7-phenylacetamido-3-bromomethyl-3-cephem-4-carboxylic acid-1-oxide, 7-phenoxyacetamido-3-bromomethyl-3-cephem-4-carboxylic acid-1-oxide, 7-formamido-3-bromomethyl-3-cephem-4-carboxylic acid-1-oxide and 7-benzamido-3-bromomethyl-3-cephem-4-carboxylic acid-1-oxide.

The process of the invention is particularly suitable for the preparation of 7-acylamino-3-(thio-substituted)-methyl-3-cephem-4-carboxylic acid-1-oxide derivatives which can be converted in known manner into known therapeutically active 3-(R-thiomethyl)-cephalosporanic acid derivatives. Accordingly, the group R in the silylated thiols of formula I is preferably a group which after exchange with the bromine atom of 7-acylamino-3-bromomethyl-3-cephem-4-carboxylic acid-1-oxide derivatives according to the process of the invention, provides corresponding 3-(R-thiomethyl) intermediates which can be converted in known manner into therapeutically active cephalosporanic acid derivatives having the same 3-(R-thiomethyl) group. However, the process of the invention is not limited to the preparation of such intermediates, but can be used for the preparation of any 7-acylamino-3-(R-thiomethyl)-3-cephem-4-carboxylic acid-1-oxide derivatives.

Suitable organic groups R are, for example, 5- or 6-membered heterocyclic groups having 1 to 4 heteroatoms. Particularly suitable are 5- or 6-membered heterocyclic groups having one or more nitrogen or sulfur atoms as the heteroatoms, which groups may be substituted by at least one member of the group consisting of lower alkyl, carboxy(lower alkyl), (lower alkyl)amino or phenyl groups. The term 'lower alkyl' as used in this specification means alkyl groups of 1 to 4 carbon atoms. Examples of specific 5- or 6-membered heterocyclic groups are imidazole, triazole, thiadiazole, tetrazole, pyrimidine, methyl-imidazole, methyl-thiadiazole, methylamino-thiadiazole, carboxymethyl-thiadiazole, methyltetrazole, phenyl-tetrazole, carboxymethyl-tetrazole and dimethyl-pyrimidine.

The 7-acylamino-3-bromomethyl-3-cephem-4-carboxylic acid-1-oxide derivatives and the carbon esters thereof which are starting materials the process of the invention are, generally speaking, known compounds, see for example, British Pat. No. 1,326,531. They can be suitably prepared by use of the methods described in European Pat. No. 0,001,149.

A number of the silyl esters of the 7-acylamino-3-bromomethyl-3-cephem-4-carboxylic acid-1-oxides which are particularly suitable for use as starting materials in the process of the invention have been described for the first time in European patent application Ser. No. 0,015,629 which discloses a convenient method for the preparation of said silyl esters as well.

A number of the silylated thiols of the formula I are new and various new members of this group of compounds as well as new methods for the preparation of these compounds have been disclosed in U.S. patent application Ser. No. 280,350 filed July 6, 1981.

This application discloses methods for the trimethylsilylation of inter alia thiols of the formula RSH, wherein R is as hereinbefore defined, with hexamethyldisilazane in the presence of catalysts of the formula X-NH-Y, wherein X and Y are the same or different and each represents an electron-withdrawing group, or X represents an electron-withdrawing group and Y represents a hydrogen atom or a trialkylsilyl group, or X and Y together represent an electron-withdrawing group which forms a cyclic system together with the nitrogen atom to which they are attached.

Suitable catalysts for use in this trimethylsilylation method are for example: trichloroacetamide, trifluoroacetamide, phthalimide, 3,4,5,6-tetrachlorophthalimide, 3,4,5,6-tetrabromophthalimide, 1,8-naphthalimide, maleimide, barbituric acid, saccharin, N-benzoyl-4-toluenesulfonamide, N-(2-methoxybenzoyl)-4-toluenesulfonamide, N-(1-naphthoyl)-4-toluenesulfonamide, N-benzoylbenzenesulfonamide, N-(2-methoxy-1-naphthoyl)-4-toluenesulfonamide, N-(2-methoxy-1-naphthoyl)methane sulfonamide, di-(4-toluenesulfonyl)-amine, dimethyl N-(trichloroacetyl)-phosphoramidate, di-4-nitrophenyl N-(trichloroacetyl)-phosphoramidate, di-4-nitrophenyl N-(4-toluene sulfonyl)-phosphoramidate, diisopropyl N-(dichloroacetyl)-phosphoramidate, di-o-chlorophenyl N-(4-chlorophenylsulfonyl)phosphoramidate, tetraphenyl imidodiphosphate, sulfamide, N,N-dimethylsulfamide, N,N'-bis-(trimethylsilyl)-sulfamide, 1,2-benzisothiazol-3(2H)-one and 4-benzoyloxy-1,2-dihydro-1-oxophthalazine.

The process for the preparation of silylated thiols of formula I by reaction of thiols of the formula R—SH, wherein R is as hereinbefore defined, with hexamethyldisilazane may be carried out with or without an organic solvent at a temperature between 0° and 150° C.

New silylated thiols of formula I which have been prepared by this method and which can be used in the process of the present invention are, for example, 2-methyl-5-trimethylsilylthio-1,3,4-thiadiazole, 1-methyl-2-trimethylsilylthioimidazole, 2-methylamino-5-trimethylsilylthio-1,3,4-thiadiazole, 1-phenyl-5-trimethylsilylthio-1H-tetrazole, 1-methyl-5-trimethylsilylthio-1H-tetrazole, 4,6-dimethyl-2-trimethylsilylthiopyrimidine, 1-trimethylsilyl-5-trimethylsilylthio-1H-1,2,3-triazole, 1-trimethylsilyl-3-trimethylsilylthio-1H-1,2,4-triazole, trimethylsilyl 5-trimethylsilylthio-1,3,4-thiadiazolyl-2-acetate and trimethylsilyl 5-trimethylsilylthio-1H-tetrazolyl-1-acetate.

Many of the 7-acylamino-3-(R-thiomethyl)-3-cephem-4-carboxylic acid-1-oxide derivatives prepared by the process of the invention can be used for the preparation of therapeutically active cephalosporins. For that purpose, a 7-acylamino-3-(R-thiomethyl)-3-cephem-4-carboxylic acid-1-oxide derivative is subjected to a reduction process to reduce the sulfoxide moiety and to a deacylation process to split off the acyl group of the 7-acylamino side chain. These conversions are well-known processes; see for example, British Pat. No. 1,326,531 and Dutch patent application Ser. No. 75,08837. The corresponding 7-amino-3-(R-thiomethyl)-3-cephem-4-carboxylic acid derivative thus obtained is then acylated in known manner with an appropriate acylation agent to provide the desired therapeutically active 7-acylamino-3-(R-thiomethyl)-3-cephem-4-carboxylic acid derivative.

In the following examples, there are described several preferred embodiments to illustrate the invention. However, it should be understood that the invention is not intended to be limited to the specific embodiments.

In the examples, (1) PMR spectra were recorded at 60 MHz unless otherwise stated; chemical shifts are reported relative to tetramethylsilane ($\delta = 0$) used as an internal standard. (2) 13C NMR spectra were taken at 20 MHz with tetramethylsilane as an internal standard. (3) IR spectra were obtained on KBr discs unless otherwise indicated. (4) Boiling points and melting points are uncorrected. (5) Quantitative HPLC analyses were performed with solutions of appropriate concentration which were prepared by standard techniques. Whenever required, the purity of the reference substance was determined by means of quantitative PMR analysis using an internal standard technique. (6) Reactions were carried out in a dry nitrogen atmosphere. A stream of nitrogen was led over the reaction mixture and, in case of catalyzed silylations with hexamethyldisilazane, the nitrogen was passed into water and used to determine the reaction time by titrating the ammonia generated in the reaction with 0.1 or 1.0 N sulfuric acid, whichever was appropriate. Other reactions were followed by thin-layer chromatography on silicagel G. (7) Solvents used were dried over 4 A molecular sieves and were of an alcohol-free grade. Solutions were dried over magnesium sulfate. (8) All evaporations were performed under reduced pressure on a rotary evaporator at a bath temperature not exceeding 35° C.

EXAMPLE 1

(a) 2.15 ml (10.3 mmoles) of hexamethyldisilazane were added to a refluxing suspension of 7.0 g (20 mmoles) of 7-phenylacetamido-3-methyl-3-cephem-4-carboxylic acid-1-oxide and 18 mg (0.1 mole) of saccharin in 400 ml of dichloromethane and after refluxing had been continued for 40 minutes, the greater part of the solid had dissolved. 10 mmoles of N-trimethylsilylsuccinimide were added thereto and the clear solution which was obtained after 10 minutes, was refluxed for another 2 hours. During this preparation of the solution of trimethylsilyl 7-phenylacetamido-3-methyl-3-cephem-4-carboxylate-1-oxide, a stream of dry nitrogen was passed over the reaction mixture.

(b) Then, 0.5 g (5 mmoles) of amidosulfonic acid was added to the solution and after cooling the reaction mixture in an ice bath, 5.0 g (28 mmoles) of N-bromosuccinimide were added after which the mixture was irradiated for 45 minutes with a 150 W tungsten lamp. After the addition of 3.5 ml (13 mmoles) of tributyl phosphite, stirring was continued for 10 minutes with ice cooling and then the reaction mixture was diluted with dichloromethane to exactly 500 ml to obtain Solution A. An excess of a solution of diazomethane in ether was added to 10 ml of Solution A and after the evolution of nitrogen had ceased, the excess was destroyed with acetic acid. The residue that remained after evaporation to dryness and which consisted of the corresponding methyl ester, was subjected to quantitative HPLC analysis whereby it was determined that Solution A contained 0.0247 mmole/ml of trimethylsilyl 7-phenylacetamido-3-bromomethyl-3-cephem-4-carboxylate-1-oxide.

(c) 9 ml of 1 N H$_2$SO$_4$ were added to 1 g (8 mmoles) of sodium 1H-1,2,3-triazole-5-thiolate in 15 ml of ethyl acetate. The ethyl acetate layer was separated and the water layer was extracted with 4 portions of 10 ml of ethyl acetate. The combined extracts were dried, filtered and concentrated to 15 ml. Then, 15 ml of dichloromethane and 5 mg (0.03 mmole) of saccharin were added thereto and, while refluxing, 2.5 ml (12 mmoles) of hexamethyldisilazane were added to the mixture. Refluxing was continued for 45 minutes and from a small sample of the clear solution thus obtained, the volatile materials were evaporated and a PMR spectrum of the residue consisting of 1-trimethylsilyl-5-trimethylsilylthio-1H-1,2,3-triazole in a solution of carbon tetrachloride was recorded: 0.31 (s, 9H); 0.48 (s, 9H); 7.46 (s, 1H). The yield of the reaction was calculated to be 96%. The remainer of the clear solution mentioned above was divided into two equal parts which were used for the conversions mentioned herebelow.

(d) A solution of 4 mmoles of 1-trimethylsilyl-5-trimethylsilylthio-1H-1,2,3-triazole in dichloromethane/ethyl acetate was added to 50 ml of Solution A obtained under (b) and the reaction was carried out in duplicate. The mixture obtained was stirred for 1 hour at room temperature and after evaporation of the solvent, the residue was subjected to quantitative HPLC analysis whereby it was determined that the solutions contained 1.25 mmole (101%) and 1.27 mmole (103%) of 7-phenylacetamido-3-(1H-1,2,3-triazolyl-5)-thiomethyl-3-cephem-4-carboxylic acid-1-oxide, respectively.

The reference substance required for the HPLC analysis was isolated as follows from a reaction as described above: The reaction mixture obtained after addition of 1-trimethylsilyl-5-trimethylsilylthio-1H-1,2,3-triazole to the solution of trimethylsilyl 7-phenylacetamido-3-bromomethyl-3-cephem-4-carboxylate-1-oxide was poured into water, while adding simultaneously a 1 N sodium hydroxide solution whereby the pH was maintained at 7.0. The dichloromethane layer was separated and replaced by ethyl acetate. The pH of the water layer was adjusted to 5.5 with 4 N sulfuric acid and the ethyl acetate layer was separated and the water layer was washed twice with ethyl acetate. Then, the product was extracted from the water layer with acetyl acetate at a pH of 2. After drying, the extract was evaporated to dryness and the product was purified by dissolving it in methanol and precipitating it again by the addition of diethyl ether.

PMR Spectrum (300 MHz, DMSO-D6): 3.55, 3.59, 3.69, 3.74 (ABq, 2H, J 14 Hz); 3.78, 3.85, 3.95, 4.02 (ABq, 2H, J 19 Hz); 3.74, 3.78, 4.23, 4.27 (ABq, 2H, J 12.5 Hz); 4.92 (d. 1H, J 4.5 Hz); 5.78 (dd, 1H, J 4.5 and 8 Hz); 7.22–7.37 (m, 5H);

IR Spectrum: 3275, 3140, 1770, 1708, 1623, 1529, 1028 cm$^{-1}$.

EXAMPLE 2

(a) 15.6 ml (0.075 mmole) of hexamethyldisilazane were added to a refluxing solution of 13.2 g (0.1 mole) of 5-mercapto-2-methyl-1,3,4-thiadiazole and 92 mg (0.5 mole) of saccharin in 25 ml of toluene and the reaction was completed after 30 minutes. Toluene was removed by distillation at normal pressure and the residue was vacuum distilled to obtain 18.63 g (91.3% yield) of 2-methyl-5-trimethylsilylthio-1,3,4-thiadiazole with a boiling point of 150°–152° C. at 15 mg Hg and the distillate solidified to a solid melting at 67°–69° C.

(b) A solution of 50 mg (0.25 mmole) of 2-methyl-5-trimethylsilylthio-1,3,4-thiadiazole in 1.4 ml of dichloromethane was added to a solution of 0.125 mmole of trimethylsilyl 7-phenylacetamido-3-bromomethyl-3-cephem-4-carboxylate-1-oxide (prepared as in Example 1a and b). After stirring for 15 minutes at room temperature, the reaction was stopped by adding 0.5 ml of acetic acid to the mixture and the residue remaining after evaporation to dryness was subjected to HPLC analysis whereby it was determined that the yield of 7-phenylacetamido-3-(2-methyl-1,3,4-thiadiazolyl-5)-thiomethyl-3-cephem-4-carboxylic acid-1-oxide was 97%.

PMR Spectra (300 MHz, DMSO-D6): 2.69 (s, 3H), 3.52, 3.58, 3.67, 3.73 (ABq, 2H, J 13 Hz); 3.70, 3.78, 3.90, 3.98 (Abq, 2H, J 18 Hz); 4.09, 4.15, 4.70, 4.76 (ABq, 2H, J 13 Hz); 4.85 (d, 1H, J 4.5 Hz); 5.80 (dd, 1H, J 4.5 Hz and 8.5 Hz); 7.32 (s, 5H), 8.34 (d, 1H, J 8.5 Hz).

EXAMPLE 3

122 mg (0.76 mmole) of hexamethyldisilazane were added to a refluxing suspension of 429 mg of 3-bromomethyl-7-phenylacetamido-3-cephem-4-carboxylic acid-1-oxide and 17 mg (0.1 mmole) of saccharin in 40 ml of dichloromethane, and after refluxing for 15 minutes, a clear solution was obtained which was cooled to room temperature. For further reactions as described herebelow, a sample of this solution containing 0.1 mmole of trimethylsilyl 3-bromomethyl-7-phenylacetamido-3-cephem-4-carboxylate-1-oxide was used in all cases.

(b) 71.2 mg (0.35 mmole) of 2-methyl-5-trimethylsilylthio-1,3,4-thiadiazole were added to a part of the solution of trimethylsilyl 3-bromomethyl-7-phenylacetamido-3-cephem-4-carboxylate-1-oxide prepared as described above.

76 mg (0.44 mmole) of potassium 2-methyl-1,3,4-thiadiazole-5-thiolate were added to another part of the said solution. Both mixtures were stirred for 1 hour with ice cooling and after evaporation to dryness, the residues were subjected to quantitative HPLC analysis whereby it was determined that the reaction with the silylated thiol resulted in a quantitative yield of 7-phenylacetamido-3-(2-methyl-1,3,4-thiadiazolyl-5)-thiomethyl-3-cephem-4-carboxylic acid-1-oxide, whereas that with the potassium salt had resulted in a yield of only 80%.

(c) To four parts of the solution of trimethylsilyl 3-bromomethyl-7-phenylacetamido-3-cephem-4-carboxylate-1-oxide prepared as described hereinabove, 0.15 mmole of 1-trimethylsilyl-5-trimethylsilylthio-1H-1,2,3-triazole in 1 ml of dichloromethane, 0.30 mmole of 1-trimethylsilyl-5-trimethylsilylthio-1H-1,2,3-triazole in 2 ml of dichloromethane, 27 mg (0.22 mmole) of sodium 1H-1,2,3-triazole-5-thiolate and 48 mg (0.39 mmole) of sodium 1H-1,2,3-triazole-5-thiolate, were added respectively. The mixtures were stirred for 1 hour with ice cooling after which they were treated as described in (b). It appeared from the HPLC analysis that the conversions to 7-phenylacetamido-3-(1H-1,2,3-triazolyl-5)-thiomethyl-3-cephem-4-carboxylic acid-1-oxide with both quantities of the silylated thiol were equal and that the yield thereof was 1.3 times as high as that of the reaction with 0.39 mmole of the sodium salt and even 2.1 times as high as that of the reaction with 0.22 mmole of the sodium salt of the thiol.

EXAMPLE 4

1.52 g (7.45 mmoles) of 2-methyl-5-trimethylsilylthio-1,3,4-thiadiazole (prepared as described in Example 2a) was added to a solution of 3.26 g of t-butyl 3-bromomethyl-7-phenylacetamido-3-cephem-4-carboxylate-1-oxide of 88% purity (5.93 mmoles) in 50 ml dichloromethane and the mixture was stirred for 1 hour at room temperature. After washing with 50 ml of a saturated sodium bicarbonate solution and then with 100 ml of water, the organic layer was dried, filtered and evaporated to dryness. The residue was triturated with diethyl ether and then the solid was filtered off and was washed with 25 ml of ether. After drying under vacuum at room temperature, it was established by quantitative HPLC analysis that the content of t-butyl 7-phenylacetamido-3-(2-methyl-1,3,4-thiadiazolyl-5)-thiomethyl-3-cephem-4-carboxylate-1-oxide of the residue (3.50 g) was 93%, thus a yield of 103% was calculated.

PMR Spectrum (CDCl$_3$): 1.54 (s, 3H); 2.69 (s, 3H); 3.42, 3.98 (ABq, 2H, J 19.5 Hz); 3.58 (s, 2H); 4.04, 4.71 (ABq, 2H, J 13.5 Hz); 4.44 (d, 1H, J 4.5 Hz); 5.94 (dd, 1H, J 4.5 and 10 Hz); 7.01 (d, 1H, J 10 Hz); 7.26 (s, 5H).

EXAMPLE 5

0.5 ml (2.4 mmoles) of hexamethyldisilazane was added to a refluxing solution of 0.432 g (3.27 mmoles) of 5-mercapto-2-methyl-1,3,4-thiadiazole and 5 mg (0.03 mmole) of saccharin in 15 ml of tolune and after refluxing for 1.5 hours, the solution was evaporated to dryness. The residue was dissolved in 20 ml of dichloromethane and 0.648 g of 7-phenylacetamido-3-bromomethyl-3-cephem-4-carboxylic acid-1-oxide with a purity of 86% (1.31 mmole) was added thereto. After the mixture had been stirred for 1 hour at room temperature, the dichloromethane was evaporated and the residue was dissolved in 25 ml of ethyl acetate. 25 ml of methanol were added thereto and the solution was then evaporated to dryness. The solid obtained was mixed with 30 ml of a 1:1 mixture of ethyl acetate and diethyl ether and the precipitate was filtered off, washed with 10 ml of the same mixture of solvents and then with 10 ml of ethyl acetate. The colorless solid was vacuum dried at room temperature to obtain 0.63 g of product which according to HPLC analysis, was 92% of 7-phenylacetamido-3-(2-methyl-1,3,4-thiadiazolyl-5)-thiomethyl-3-cephem-4-carboxylic acid-1-oxide, which amounts to a yield of 93%.

EXAMPLE 6

0.55 ml (2.6 mmoles) of hexamethyldisilazane was added to a refluxing solution of 0.46 g (3.5 mmoles) of 5-mercapto-2-methyl-1,3,4-thiadiazole and 5 mg (0.03 mmole) of saccharin in 25 ml of toluene. After refluxing for 1.5 hours, the volatile materials were evaporated and the residue was dissolved in a mixture of 25 ml of dichloromethane and 10 ml of acetonitrile.

0.60 g (1.66 mole) of 7-formamido-3-bromomethyl-3-cephem-4-carboxylic acid-1-oxide (purity 93%) was added to the solution and the mixture was stirred for one hour. The mixture was evaporated to dryness and 10 ml of methanol were added to the residue. After evaporation of the methanol, 50 ml of diethyl ether were added to the solid residue and the solid was filtered, washed with diethyl ether, 75 ml of a 10% solution of methanol in ether and with 40 ml of a 25% solution of methanol in ether. The product was dried in vacuo at room temperature to obtain 0.63 g (97.6%) of 7-formamido-3-(2-methyl-1,3,4-thiadiazolyl-5)-thiomethyl-3-cephem-4-carboxylic acid-1-oxide.

PMR Spectrum) (DMSO-D6): 2.67 (s, 3H); 3.88 (s, 2H); 4.09 and 4.71 (ABq, 2H, J 13.5 Hz); 4.89 (d, 1H, J 4.5 Hz); 5.83 and 5.98 (dd, 1H, J 4.5 and 9 Hz); 8.12 (s, 1H); 8.28 (d, 1H, J 9 Hz).

IR Spectrum: 3295, 1785, 1713, 1658, 1635, 1529, 1225, 1001, 993 cm$^{-1}$.

EXAMPLE 7

0.56 g (1.0 mmole) of t-butyl 7-benzamido-3-bromomethyl-3-cephem-4-carboxylate-1-oxide (purity 84%) and 15 ml of dichloromethane were added to 0.63 g (3 mmoles) of 2-methyl-5-trimethylsilylthio-1,3,4-thiadiazole, prepared as described in Example 6, and the reaction was complete after stirring for 5 minutes at room temperature. After stirring for 15 minutes, the reaction mixture was evaporated to dryness and 10 ml of toluene and 1 ml of methanol were added thereto, after which the mixture was evaporated to dryness again. The remaining solid was washed on a sintered glass funnel with diethyl ether with 2 portions of 5 ml of 0.1 N HCl and with 10 ml of diethyl ether. The product was vacuum dried at room temperature to obtain 0.53 g (102%) of t-butyl 7-benzamido-3-(2-methyl-1,3,4-thiadiazolyl-5)-thiomethyl-3-cephem-4-carboxylate-1-oxide.

PMR Spectrum (CDCl$_3$): 1.56 (s, 9H); 2.67 (s, 3H); 3.54 and 4.08 (ABq, 2H, J 18 Hz); 4.07 and 4.70 (ABq, 2H, J 13.5 Hz); 4.64 (d, 1H, J 4.5 Hz); 6.10 and 6.25 (dd, 1H, J 4.5 and 9 Hz); 7.2–7.8 (m, 6H).

IR Spectrum: 3390, 3060, 1790, 1771, 1710, 1670, 1648, 1602, 1580, 1520, 1153, 1063 cm$^{-1}$.

EXAMPLE 8

171 mg (0.84 mmole) of 2-methyl-5-trimethylsilylthio-1,3,4-thiadiazole were added to a solution of 226 mg (0.49 mmole) of methyl 7-phenoxyacetamido-3-bromomethyl-3-cephem-4-carboxylate-1-oxide in 25 ml of dichloromethane and the mixture was stirred for 2.5 hours at room temperature. The solvent was evaporated and a solution of 0.25 ml of ethanol in 25 ml of diethyl ether was added to the residue. The solid was collected by filtration, washed twice with 5 ml of ether, twice with 5 ml of 0.1 N hydrochloric acid and 5 ml of ether. The product was vacuum dried at room temperature to obtain 230 mg (91.6%) of methyl 7-phenoxyacetamido-3-(2-methyl-1,3,4-thiadiazolyl-5)-thiomethyl-3-cephem-4-carboxylate-1-oxide.

PMR Spectrum (DMSO-D6): 2.65 (s, 3H); 3.61 (s, 3H); 3.79 (s, 2H); 4.00 and 4.72 (ABq, 2H, J 13.5 Hz); 4.61 (s, 2H); 4.90 (d, 1H, J 4.5 Hz); 5.88 and 6.05 (dd, 1H, J 4.5 and 9 Hz); 6.8–7.4 (m, 5H); 8.05 (d, 1H, J 9 Hz).

IR Spectrum: 3392, 3037, 2849, 1777, 1718, 1694, 1633, 1600, 1515, 1438, 1235, 1062 cm$^1$.

EXAMPLE 9

A mixture consisting of 0.172 g (1.50 mmole) of 2-mercapto-1-methylimidazole, 5 mg (0.027 mmole) of saccharin, 15 ml of toluene and 0.63 ml (3.0 mmoles) of hexamethyldisilazane was refluxed for one hour and then volatile materials were evaporated. The residue was dissolved in 10 ml of dichloromethane and the solution of 1-methyl-2-trimethylsilylthioimidazole thus prepared was cooled in an ice bath while 493 mg (0.95 mmole) of t-butyl 7-phenylacetamido-3-bromomethyl-3-cephem-4-carboxylate-1-oxide (purity 93%) was added thereto. After stirring for 1 minute, 2 ml of ethanol were added and the reaction mixture was evaporated to dryness. The colorless residue was transferred to a sintered glass funnel with diethyl ether and excess of thiol was removed with ether (20 times-10 ml), 2% of methanol in ether (5 times-10 ml) and 5% methanol in ether (twice-10 ml) to obtain 0.54 g (95%) of the hydrobromide salt of t-butyl 7-phenylacetamido-3-(1-methylimidazolyl-2)-thiomethyl-3-cephem-4-carboxylate-1-oxide.

PMR Spectrum (CDCl$_3$): 1.34 (s, 9H); 3.66 (s, 2H); 3.71 and 4.11 (ABq. 2H, J 17 Hz); 3.94 (s, 3H); 4.20 and 4.71 (ABq, 2H, J 18 Hz); 5.46 (d, 1H, J 4.5 Hz); 5.84 and 6.00 (dd, 1H, J 4.5 and 9 Hz); 7.01 (d, 1H, J 9 Hz); 7.23 (s, 5H); 7.30 (d, 1H, J 1.5 Hz); 7.51 (d, 1H, J 1.5 Hz); 8.0 (broad s, about 1H).

IR Spectrum: 3400, 1790, 1711, 1675, 1510, 1150, 1008 cm$^{-1}$.

EXAMPLE 10

(a) 0.58 ml (2.8 mmoles) of hexamethyldisilazane was added to a refluxing suspension of 303 mg (3.0 mmoles) of 3-mercapto-1H-1,2,4-triazole and 2.0 mg (0.004 mmole) of di-4-nitrophenyl N-(4-toluenesulfonyl)-phosphoramidate in 5 ml of dichloromethane, and refluxing was continued for 90 minutes and then the solution was cooled to room temperature.

(b) 0.23 ml (1.15 mmole) of hexamethyldisilazane was added to a suspension of 653 mg of 7-phenylacetamido-3-bromomethyl-3-cephem-4-carboxylic acid-1-oxide with a content of 86% (1.31 mmole) in 20 ml of dichloromethane, and the mixture was stirred for 45 minutes at room temperature which resulted in a light-yellow, almost clear solution.

(c) The solution of 1-trimethylsilyl-3-trimethylsilylthio-1H-1,2,4-triazole prepared under (a) was added to the solution of the trimethylsilyl ester prepared in (b) and the mixture was stirred for one hour at room temperature. The solvent was evaporated and 10 ml of ethyl acetate and then 10 ml of diethyl ether which first had been saturated with water were added to the residue. The precipitate was filtered off and was washed with 20 ml of a 3:1 mixture of ethyl acetate and diethyl ether. The dried solid was further treated as described in Example 7 to obtain 0.61 g of pure 7-phenylacetamido-3-(1H-1,2,4-triazolyl-3)-thiomethyl-3-cephem-4-carboxylic acid-1-oxide.

PMR Spectrum (DMSO-D6): 3.63 (s, 2H); 3.83 (s, 2H); 3.81, 4.04, 4.48, 4.72 (ABq, 2H, J 13.5 Hz); 4.83 (d, 1H, J 4.5 Hz); 5.78 (dd, 1H, J 4.5 and 7.5 Hz); 7.27 (s, 5H); 8.78 (d, 1H, J 7.5 Hz).

IR Spectrum: 3285, 1775, 1703, 1642, 1520, 1491, 1220, 1028 cm$^1$.

EXAMPLE 11

(a) 0.2 ml (0.96 mmole) of hexamethyldisilazane was added to a suspension of 502 mg of 7-phenylacetamido-3-bromomethyl-3-cephem-4-carboxylic acid-1-oxide (with a content of 86%) in 20 ml of dichloromethane and the mixture was stirred for 45 minutes at room temperature to obtain a clear solution.

(b) A solution was prepared from 163 mg (1.10 mmole) of 2-methylamino-5-mercapto-1,3,4-thiadiazole and 2 mg (0.04 mmole) of tetraphenyl imidodiphosphate in 20 ml of ethyl acetate and then, 0.22 ml (1.06 mmole) of hexamethyldisilazane was added thereto. The mixture was refluxed for 45 minutes and then concentrated to 5 ml and this solution of 2-methylamino-5-trimethylsilylthio-1,3,4-thiadiazole was added to the solution of the trimethyl ester prepared under (a). The mixture was stirred at room temperature for 30 minutes and then, 20 ml of methanol were added. The mixture was evaporated to dryness and the solid obtained was treated as described in Example 7 to obtain 0.49 g of 7-phenylacetamido-3-(2-methylamino-1,3,4-thiadiazolyl-5)-thiomethyl-3-cephem-4-carboxylic acid-1-oxide which contained about 1 mole of water according to the NMR spectrum.

PMR Spectrum (DMSO-D6): 2.97 (s, 3H); 3.64 (s, 2H); 3.88 (s, 2H); 4.03 and 4.53 (ABq, 2H, J 13.5 Hz); 4.91 (d, 1H, J 4.5 Hz); 5.76 and 5.90 (dd, 1H, J 4.5 and 8.5 Hz); 7.33 (s, 5H); 8.35 (d, 1H, J 8.5 Hz).

IR Spectrum: 3285, 1780, 1718, 1625, 1515, 1030 cm$^{-1}$.

EXAMPLE 12

(a) 1.5 ml (7.2 mmoles) of hexamethyldisilazane were added to a refluxing mixture of 0.88 g (5.0 mmoles) of 5-mercapto-1,3,4-thiadiazolyl-2-acetic acid, 5.0 mg (0.027 mmole) of saccharin and 25 ml of toluene and after refluxing for 2 hours, the solvent and excess of hexamethyldisilazane were evaporated to obtain 1.60 g (100%) of trimethylsilyl 5-trimethylsilylthio-1,3,4-thiadiazolyl-2-acetate melting at 38°–42° C.

PMR Spectrum (CCl4): 0.33 (s, 9H); 0.60 (s, 9H); 3.73 (s, 2H).

(b) 0.50 g (1.0 mmole) of 7-phenylacetamido-3-bromomethyl-3-cephem-4-carboxylic acid-1-oxide (purity 86%) was silylated by stirring in 15 ml of dichloromethane with 0.2 ml (0.96 mmole) of hexamethyldisilazane for 1 hour at room temperature. The trimethylsilyl 5-trimethylsilylthio-1,3,4-thiadiazolyl-2-azcetate prepared in (a) was added thereto and the mixture was stirred for 1 hour at room temperature. Volatile material was evaporated and diethyl ether was added to the residue. The solid was filtered and was washed with diethyl ether. The 0.70 g of solid obtained was dissolved in a phosphate buffer of pH 7.3, and 150 ml of ethyl acetate were added thereto. The mixture was acidified to a pH of 2.5 with 1 N HCl and the ethyl acetate layer was separated. The water layer was extracted 7 times with 150 ml of ethyl acetate, and the combined extracts were dried, filtered and evaporated. The residue was dried in vacuo at room temperature to obtain 0.48 g (92% yield) of 7-phenylacetamido-3-(2-carboxymethyl-1,3,4-thiadiazolyl-5)-thiomethyl-3-cephem-4-carboxylic acid-1-oxide.

PMR Spectrum (DMSO-D6): 3.64 (s, 2H); 3.88 (s, 2H); 4.13 and 4.83 (ABq, 2H, J 13.5 Hz); 4.20 (s, 2H); 4.86 (d, 1H, J 4.5 Hz); 5.75 and 5.90 (dd, 1H, J 4.5 and 9 Hz); 7.33 (s, 5H); 8.35 (d, 1H, J 9 Hz).

IR Spectrum: 3280, 1783, 1780, 1648, 1520, 1235, 1030 cm$^{-1}$.

EXAMPLE 13

(a) 1.78 g (10 mmoles) of 1-phenyl-5-mercapto-1H-tetrazole was silylated with 2.6 ml of hexamethyldisilazane (12.4 mmoles) in 50 ml of 1,2-dichloroethane at reflux with the reaction being catalyzed with 5 mg (0.03 mmole) of saccharin and the calculated amount of ammonia had been evolved after 20 minutes. After refluxing had been continued for another 10 minutes, the solvent and excess hexamethyldisilazane were evaporated. The residue was vacuum dried at room temperature to obtain 2.58 g (108%) of 1-phenyl-5-trimethylsilylthio-1H-tetrazole melting at 67°–68° C.

PMR Spectrum (CCl4): 0.68 (s, 9H); 7.38–7.64 (m, 3H); 7.91–8.17 (m, 2H).

(b) 0.2 ml (0.96 mmole) of hexamethyldisilazane was added to a suspension of 294.4 mg of 3-bromomethyl-7-phenylacetamido-3-cephem-4-carboxylic acid-1-oxide with a content of 81% (0.558 mmole) in 39 ml of dichloromethane and after stirring for 1.5 hour at room temperature, 314 mg (1.25 mmole) of 1-phenyl-5-trimethylsilylthio-1H-tetrazole were added to the clear light-yellow solution obtained. The conversion had been completed after stirring for 5 minutes and the reaction mixture was evaporated to dryness. The residue was subjected to HPLC analysis and the yield of 7-phenylacetamido-3-(1-phenyl-1H-tetrazolyl-5)-thiomethyl-3-cephem-4-carboxylic acid-1-oxide was found to be 102%. The reference substance for the HPLC analysis was prepared in a separate experiment using the method of described at the end of Example 1.

PMR Spectrum (DMSO-D6): 3.66 (s, 2H); 3.56, 3.88, 3.93, 4.25 (ABq, 2H, J 19 Hz); 4.12, 4.35, 4.79, 5.01 (ABq, 2H, J 13.5 Hz); 4.89 (d, 1H, J 4.5 Hz); 5.90 (dd, 1H, J 4.5 and 9 Hz); 7.38 (s, 5H); 7.74 (s, 5H); 8.43 (d, 1H, J 9 Hz).

IR Spectrum: 3295, 1788, 1773, 1712, 1660, 1516, 1498, 1240, 1002 cm$^{-1}$.

EXAMPLE 14

(a) 0.582 g (5.0 mmoles) of 5-mercapto-1-methyl-1H-tetrazole and 5.0 mg (0.03 mmole) of saccharin were dissolved in a mixture of 12 ml of ethyl acetate and 25 ml of dichloromethane and the mixture was refluxed while 1.26 ml of hexamethyldisilazane (5.5 mmoles) were added thereto. The evolution of ammonia stopped after one hour and the volatile material was evaporated, to obtain 0.94 g of 1-methyl-5-trimethylsilylthio-1H-tetrazole.

PMR Spectrum (CCl4): 0.61 (s, 9H) and 3.79 (s, 3H).

(b) In the manner described in Example 13b, 240 mg of 3-bromomethyl-7-phenylacetamido-3-cephem-4-carboxylic acid-1-oxide with a content of 81% (0.455 mmole) were silylated with hexamethyldisilazane and 0.19 g (1.01 mmole) of 1-methyl-5-trimethylsilylthio-1H-tetrazole was added to the solution obtained. After stirring for 30 minutes at room temperature, HPLC analysis was carried out and it was found that the yield of 7-phenylacetamido-3-(1-methyl-1H-tetrazolyl-5)-thiomethyl-3-cephem-4-carboxylic acid-1-oxide was 91%. The reference substance for the HPLC analysis was prepared in a separate experiment using the method described at the end of Example 1.

PMR Spectrum (300 MHz, DMSO-D6): 3.53, 3.58, 3.67, 3.72 (ABq, 2H, J 14.5 Hz); 3.71, 3.77, 3.92, 3.98 (ABq, 2H, J 19 Hz); 3.92 (s, 1H); 4.13, 4.18, 4.58, 4.63 (ABq, 2H J 13.5 Hz); 4.85 (d, 1H, J 4.5 Hz); 5.80 (dd, 1H, J 4.5 and 8 Hz); 7.22–7.35 (m, 5H); 8.38 (d, 1H, J 8 Hz).

IR Spectrum: 3395, 1785, 1708, 1523, 1508, 1497, 1250, 1011 cm$^{-1}$.

EXAMPLE 15

A solution of 5 mmoles of 1-methyl-5-trimethylsilylthio-1H-tetrazole in 25 ml of dichloromethane, prepared as described in Example 14a, was added to a suspension of 0.38 g (0.99 mmole) of 93% 7-formamido-3-bromomethyl-3-cephem-4-carboxylic acid-1-oxide in 20 ml of acetonitrile and after stirring for 3 hours in an ice bath, the reaction was complete. The product was isolated as its methyl ester in the following way. An ethereal solution of diazomethane was added, followed by 10 ml of methanol. After the evolution of nitrogen had stopped, excess diazomethane was destroyed with acetic acid and volatile materials were evaporated. Diethyl ether was added to the residue and the solid was filtered, washed with ether and dried under vacuum at room temperature to obtain 0.37 g (97.3%) of methyl 7-formamido-3-(1-methyl-1H-tetrazolyl-5)-thiomethyl-3-cephem-4-carboxylate-1-oxide.

PMR Spectrum (DSMO-D6): 3.83 (s, 3H); 3.95 (s, 5H); 4.11 and 4.70 (ABq, 2H, J 9 Hz); 4.95 (d, 1H, J 4.5); 5.93 and 6.10 (dd, 1H, J 4.5 and 9 Hz); 8.22 (s, 1H); 8.45 (d, 1H, J 9 Hz).

IR Spectrum: 3290, 1775, 1720, 1670, 1520, 1240, 1170, 1028 cm$^{-1}$.

EXAMPLE 16

1.6 ml of hexamethyldisilazane (7.5 mmoles) were added to a refluxing suspension of 809 mg (5 mmoles) of 5-mercapto-1H-tetrazolyl-1-acetic acid and 10 mg (0.06 mmole) of saccharin in 25 ml of toluene and refluxing was continued for 1.5 hours. The solvent and excess hexamethyldisilazane were evaporated and the residue was dissolved in 20 ml of dichloromethane. To this solution of trimethylsilyl 5-trimethylsilylthio-1H-tetrazolyl-1-acetate, 485 mg of t-butyl 7-phenylacetamido-3-bromomethyl-3-cephem-4-carboxylate-1-oxide (93% purity, 0.93 mmole) were added and the mixture was stirred for 2 hours at room temperature. The product was converted to its methyl ester as described in Example 15. The solvents were evaporated and the residue was taken up in 75 ml of ethyl acetate and 25 ml of water. The ethyl acetate layer was separated and the water layer was extracted with 50 ml of ethyl acetate. The combined extracts were dried, filtered and evaporated to dryness. The residual oil was triturated with diethyl ether and the solid obtained was collected by filtration, was washed with ether and dried in vacuo to obtain 0.49 g (96.8%) of t-butyl 7-phenylacetamido-3-(1-carboxymethyl-1H-tetrazolyl-5)-thiomethyl-3-cephem-4-carboxylate-1-oxide.

PMR Spectrum (CDCl₃): 1.53 (s, 9H); 3.32 and 3.89 (ABq, 2H, J 18 Hz); 3.55 (s, 2H); 3.75 (s, 3H); 4.09 and 4.52 (ABq. 2H, J 13.5 Hz); 4.42 (d, 1H, J 4.5 Hz); 4.99 (s, 2H); 5.83 and 5.99 (dd, 1H, J 4.5 and 9 Hz); 6.88 (d, 1H, J 9 Hz); 7.21 (s, 5H).

IR Spectrum: 3325, 1785, 1753, 1712, 1658, 1522, 1240, 1153, 1040 cm⁻¹.

EXAMPLE 17

0.63 ml (3.0 mmoles) of hexamethyldisilazane was added to a refluxing mixture of 0.21 g (1.5 mmole) of 4,6 dimethyl-2-mercaptopyrimidine, 5 mg (0.01 mmole) of di-4-nitrophenyl N-(4-toluenesulfonyl)phosphoramidate and 10 ml of toluene and refluxing was continued for 1.5 hours. Then the toluene and excess hexamethyldisilazane were evaporated and the residue was dissolved in 10 ml of dichloromethane. The solution of 4,6-dimethyl-2-trimethylsilylthiopyrimidine thus obtained, a solution of 143 mg (0.23 mmole) of trichloroethyl 7-phenoxyacetamido-3-bromomethyl-3-cephem-4-carboxylate-1-oxide (purity 92%) in 10 ml of dichloromethane was added with ice cooling and the reaction was complete within 2 minutes. After stirring for 15 minutes more, 2 ml of ethanol were added and the mixture was evaporated to dryness. The product was separated from excess thiol by dissolving it in 50 ml of phosphate buffer of pH 8.0 which was layered with 100 ml of ethyl acetate. The organic layer was separated and the water layer was extracted with 3 portions of 30 ml of ethyl acetate. The combined extracts were dried, filtered and evaporated to dryness. The residue was triturated with diethyl ether and the solid was collected by filtration and was washed with ether. The product was vacuum-dried at room temperature to obtain 0.13 g (89%) of trichloroethyl 7-phenoxyacetamido-3-(4,6-dimethylpyrimidinyl-2)-thiomethyl-3-cephem-4-carboxylate-1-oxide.

PMR Spectrum (CDCl₃+3 drops of DMSO-D6): 2.40 (s,6H); 3.74 and 4.02 (ABq, 2H, J 11 Hz); 4.08 and 4.81 (ABq, 2H, J 15 Hz); 4.59 (s, 2H); 4.90 (d, 1H, J 4.5 Hz); 4.91 and 5.14 (ABq, 2H, J 12 Hz); 6.05 and 6.22 (dd, 1H, J 4.5 and 10 Hz); 6.77–7.54 (m, 6H); 8.07 (d, 1H, J 10 Hz).

IR Spectrum: 3375, 1788, 1738, 1698, 1630, 1600, 1581, 1520, 1494, 1242, 1172, 1021 cm⁻¹.

Various modifications of the process of the invention may be made without departing from the spirit or scope thereof and it is to be understood that the invention is intended to be limited only as defined in the appended claims.

What is claimed is:

1. A process for the preparation of 7-acylamino-3-(thiosubstituted)-methyl-3-cephem-4-carboxylic acid-1-oxide derivatives comprising reacting a 7-acylamino-3-bromomethyl-3-cephem-4-carboxylic acid-1-oxide derivative with a silylated thiol of the formula

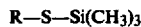

R—S—Si(CH₃)₃ wherein R is a 5- or 6-membered heterocyclic group having at least one nitrogen or sulfur atom as the heteroatoms to obtain the corresponding 7-acylamino-3-(R-thiomethyl)-3-cephem-4-carboxylic acid-1-oxide derivative.

2. The process of claim 1 wherein the reaction is carried out at a temperature between −20° and 80° C.

3. The process of claim 2 wherein the reaction is carried out at a temperature between 0° and 50° C.

4. The process of claim 1 or 3 wherein the reaction is carried out in the presence of an inert organic solvent.

5. The process of claim 1 wherein the heterocyclic group is substituted by at least one member of the group consisting of lower alkyl, carboxy(lower alkyl), (lower alkyl)amino and phenyl.

6. The process of claim 1 wherein the heterocyclic group is selected from the group consisting of imidazole, triazole, thiadiazole, tetrazole, pyrimidine, methylimidazole, methyl-thiadiazole, methylaminothiadiazole, carboxymethylthiadiazole, methyl-tetrazole, phenyl-tetrazole, carboxymethyltetrazole and dimethyl-pyrimidine.

* * * * *